(12) United States Patent
Takuma et al.

(10) Patent No.: US 6,900,298 B2
(45) Date of Patent: May 31, 2005

(54) PROCESS FOR PRODUCING NUCLEIC ACID DERIVATIVE

(75) Inventors: Yuki Takuma, Kanagawa (JP); Kyoko Endo, Kanagawa (JP); Takeshi Murakami, Kanagawa (JP); Tomoko Maeda, Kanagawa (JP); Tomoko Sasaki, Kanagawa (JP); Youichi Matsumoto, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/361,593

(22) Filed: Feb. 11, 2003

(65) Prior Publication Data

US 2003/0153745 A1 Aug. 14, 2003

(30) Foreign Application Priority Data

Feb. 12, 2002 (JP) ...................................... 2002-033514
Feb. 14, 2002 (JP) ...................................... 2002-036204

(51) Int. Cl.$^7$ ................................................ C07H 1/00
(52) U.S. Cl. ...................... 536/22.1; 536/28.1; 536/28.7
(58) Field of Search .............................. 536/22.1, 28.1, 536/28.7, 27.11

(56) References Cited

FOREIGN PATENT DOCUMENTS

CN            1216766        5/1999

OTHER PUBLICATIONS

U. Niedballa, et al., "A General Synthesis of N–Glycosides. I.[1] Synthesis of Pyrimidine Nucleosides", J. Org. Chem., vol. 39, No. 25, 1974, pp. 3654–3663.

Helmut Vorbrueggen, et al., "Nucleoside Synthesis with Trimethylsilyl Triflate and Perchlorate as Catalysts[2)]", Chem. Ber., vol. 114, 1981, pp. 1234–1255.

Carol Cristescu, et al., "A Simplified Method for the Synthesis of 1,2,4–Triazole Nucleosides and 1,2,4–Triazine-Nucleosides", Revue Roumaine De Chimie, vol. 32, No. 3, 1987, pp. 329–333.

Bunji Shimizu, et al., "The Synthesis of Ara–C via β–D–Xylofuranosylcytosine Derivatives and of "Virazole" By The Trimethylsilyl Ether "Solution" Method", Nucleic Acid Chemistry, vol. 1, 1978, pp. 255–260.

C. S. Hudson, et al., "The Isomeric Tetracetates of ι–Arabinose and Beta–Triacetyl–Methyl–ι–Arabinoside", J. Am. Chem. Soc, vol. 40, 1918, pp. 992–997.

H. Jin, et al., Tetrahedron: Asymmetry, vol. 4, No. 2, XP–001145857, pp. 211–214, "Unexpected Effects of Lewis Acids in the Synthesis of Optically Pure 2'–Deoxy–3'–Oxacytidine Nucleoside Analogues", 1993.

*Primary Examiner*—Elli Peselev
(74) *Attorney, Agent, or Firm*—Oblon, Spivak, McClelland, Maier & Neustadt, P.C.

(57) ABSTRACT

A process for efficiently producing a nucleic acid derivative by condensing a specific nitrogen-containing heterocyclic compound such as a dinitrogen 6-membered heterocyclic compound or a trinitrogen 5-membered heterocyclic compound with a pentose using a less expensive and safe reagent. Namely, a process for producing a nucleic acid derivative by condensing a dinitrogen 6-membered heterocyclic compound or a trinitrogen 5-membered heterocyclic compound with a pentose in the presence of an iron halide.

12 Claims, No Drawings

PROCESS FOR PRODUCING NUCLEIC ACID DERIVATIVE

FIELD OF THE INVENTION

This invention relates to a process for producing a nucleic acid derivative having a specific nitrogen containing heterocycle as a base. Such nucleic acid derivatives are important compounds which are useful as nucleic acid-based antiviral agents or intermediates for synthesizing the same.

BACKGROUND ART

Various discussions have been made on the production of nucleic acid derivatives. It is general to use a process wherein a base and a sugar are condensed with the use of a Lewis acid catalyst, in particular, the process wherein $SnCl_4$ or trimethylsilyl trifluoromethanesulfonate is used as the Lewis acid catalyst.

As an example of such process with the use of a uracil derivative as the base, it is known to condense acylated ribose with azauracil (J. Org. Chem., Vol. 39, p. 3654-3663 (1974)). From the viewpoint of industrial production, however, this process has some problems such that $SnCl_4$ and $ZnCl_2$ which are regarded as favorable Lewis acid catalysts are expensive reagents and attention should be paid to the removal of the residues of these catalysts containing heavy metals such as Sn and Zn in case of producing intermediates for pharmaceuticals.

Moreover, Published Chinese Patent Application No. 1216766 discloses condensation of 1,2,3,5-tetra-O-acetyl-β-ribofuranose with 5-methyluracil and it is generally described that various Lewis acids are usable therefore. However, only $SnCl_4$ was employed and this process suffers from the same problems in the industrial production.

As examples with the use of a triazole derivative as a base, there are known processes reported in Chem. Ber., vol. 114, p. 1234–1255 (1981), Revue Roumaine de Chimie, vol. 32, p. 329–333 (1987) and Nucl. Acid. Chem., vol. 1, p. 255–260 (1978). In each of these cases, use is exclusively made of trimethylsilyl trifluoromethanesulfonate, trimethylsilane iodide or mercury chloride as the Lewis acid.

In case of condensing sugar as intermediates for pharmaceuticals or agricultural chemicals, stereoselective production is carried out. In such a process, it is preferable from an industrial viewpoint to re-use stereoisomers other than the desired one. In case of condensing a nucleic acid derivative, a β-anomer is most frequently employed. Thus, it is industrially favorable that a β-anomer can be conveniently obtained by isomerizing the undesired α-anomer, if possible. Moreover, it is difficult to obtain starting materials of sugars having 1,2-cis configuration. Therefore, it has been required to establish a method of industrially effectively obtain these materials from stereoisomers thereof which can be more easily obtained.

As a process for isomerizing (epimerizing) a stereoconfiguration on the carbon atom at the 1-position of a sugar, there has been known only one process whereby pentaacetyl-β-mannose which is a 6-membered sugar is isomerized in the presence of acetic anhydride and zinc chloride (J. Am. Chem. Soc., 40, 992 (1918)). In this process, zinc chloride which is a Lewis acid is used as a catalyst in the reaction. Thus, there arise some problems such that the reagent is poor in handling properties due to its high hygroscopicity and troublesome procedures are needed in the isolation and purification after the completion of the reaction. Namely, this process is not favorable from an industrial viewpoint.

SUMMARY OF THE INVENTION

To obtain a nucleic acid derivative by condensing a base with a sugar as described above, it has been required to develop an efficient condensation process with the use of a less expensive and safe reagent. In addition, it has been required to develop a process for conveniently isomerize (epimerize) the stereoconfiguration on the carbon atom at the 1-position of a pentose to be used in the condensation reaction.

The present inventors have conducted intensive studies to solve the problems discussed above. As a result, they have successfully found out that, in condensing a specific nitrogen-containing heterocyclic compound with a pentose, the desired condensation can be efficiently performed by using an iron halide as a catalyst, thereby completing the invention.

Accordingly, the gist of the invention resides in a process for producing a nucleic acid which comprises condensing a dinitrogen 6-membered heterocyclic compound or a trinitrogen 5-membered heterocyclic compound with a pentose in the presence of an iron halide, and a process for producing a nucleic acid derivative which comprises isomerizing a pentose at the anomeric position in the presence of an acid anhydride and a sulfonic acid to give a desired configuration at the anomeric position and then subjecting it to the condensation reaction as described above.

DETAILED DESCRIPTION OF THE INVENTION

Now, the present invention will be illustrated in greater detail.

The production process according to the present invention comprises condensing a specific nitrogen-containing heterocyclic compound such as a dinitrogen 6-membered heterocyclic compound or a trinitrogen 5-membered heterocyclic compound with a pentose in the presence of an iron halide to give a nucleic acid derivative.

(Nitrogen-containing Heterocyclic Compound)

The nitrogen-containing heterocyclic compound to be used in the invention is either a dinitrogen 6-membered heterocyclic compound or a trinitrogen 5-membered heterocyclic compound.

Examples of the dinitrogen 6-membered heterocyclic compound include compounds having a pyridazine ring, a pyrimidine ring or a pyrazine ring as the heterocyclic skeleton, and compounds having a pyridazinone ring, a pyridadinedione ring, a pyrimidinone ring, a pyrimidinedione ring or a dehydropyrimidinedion ring in which the carbon atom(s) constituting the above-described ring form a carbonyl group.

Examples of the trinitrogen 5-membered heterocyclic compound include compounds having a triazole ring as the heterocyclic skeleton.

These dinitrogen 6-membered heterocyclic compound and trinitrogen 5-membered heterocyclic compound may have arbitrary substituent(s) on the skeleton. The substituents are not restricted so long as they remain inactive during the condensation reaction. Specific examples include halogen atom such as a fluorine atom, a chlorine atom and a bromine atom; a cyano group; a formyl group; a carbamoyl group; carbonate groups such as a methoxycarbonyl group, an ethoxycarbonyl group, a benzyloxycarbonyl group and a phenoxycarbonyl group; acyl groups such as an acetyl group and a benzoyl group; optionally substituted amino groups such as an amino group, a methylamino group and a dimethylamino group; and optionally substituted alkyl groups such as a methyl group, an ethyl group, a propyl group, an isopropyl group, a benzyl group and a trifluoromethyl group.

It is preferable that the carboxylic ester groups, the acyl groups, the optionally substituted amino groups and the optionally substituted alkyl groups have each 4 or less carbon atoms, still preferably 2 or less carbon atoms.

It is preferable that the dinitrogen 6-membered heterocyclic compound is a compound represented by the general formula (A) or (A'), while it is preferable that the trinitrogen 5-membered heterocyclic compound is a compound represented by the general formula (B) or (B').

In the formulae, $R^1$ preferably represents a cyano group, a carbamoyl group, an alkoxycarbonyl group having 4 or less carbon atoms, an amino group or an alkyl group having from 1 to 4 carbon atoms, particularly preferably a methyl group or an ethyl group.

n is an integer of 0 to 2, preferably 0 or 1.

In case where n is 2, a plural number of $R^1$s may be different from each other, and two $R^1$s adjacent to each other may form together a carbon ring or a heterocycle. Preferable examples of the ring include a cyclopentane ring, a cyclohexane ring, a benzene ring, an imidazole ring, a pyrazine ring and a pyrimidine ring which may be substituted by the substituent(s) as cited above.

In case where the dinitrogen 6-membered heterocyclic compound or the trinitrogen 5-membered heterocyclic compound has an unsubstituted or mono-substituted amino group or the carbon atoms constituting the ring form a carbonyl group, it is preferable to silylate them prior to the condensation reaction. More specifically speaking, a compound represented by the general formula (A) or (B) is usually derived into the corresponding compound (A') or (B') by preliminarily silylating at the oxygen in the carbonyl group or a nitrogen atom and then subjected to the condensation with a pentose. In this case, the compound (A') or (B') may be used after isolation and purification. Alternatively, the compound after the completion of the silylation as it is may be used to the reaction with the pentose.

In the general formula (A') and (B'), $G^1$ to $G^6$ each independently represent an alkyl group, preferably an alkyl group having from 1 to 4 carbon atoms. Specific examples of the silyl group to be introduced include a trimethylsilyl group, a t-butyldimethylsilyl group and a triethylsilyl group. A trimethylsilyl group or a triethylsilyl group is preferable and a trimethylsilyl group is still preferable.

The silylation method is not particularly restricted, so long as it is a method commonly employed in silylating a hydroxy group or an amino group. For example, the compound (A) or (B) is refluxed in 1,1,1,3,3,3-hexamethyldisilazane, which is a silylating agent, in the presence of a small amount of ammonium sulfate for several hours and then the excessive 1,1,1,3,3,3-hexamethyldisilazane is distilled off.

(Pentose)

Examples of the pentose include aldopentoses such as ribose and arabinose, ketopentoses such as ribose, and pentose derivatives in which part of the hydroxyl groups (preferably at the 2- or 3-position, still preferably at the 2-position) are substituted by a halogen atom or a hydrogen atom. Among these compounds, aldopentoses such as ribose and arabinose are preferable and ribose is still preferable.

As the pentose, use may be made of either a D-enantiomer, an L-enantiomer or a mixture thereof. Such a pentose occurs as α- and β-anomers as isomers at the anomeric position. Use may be made of either of these isomers or a mixture thereof.

The pentose described above is used to the condensation reaction after protecting the hydroxyl group.

Protective groups for the hydroxyl groups are not particularly restricted. Preferable examples of the protective group for the hydroxyl group at the anomeric position include acyl groups such as an acetyl group, a chloroacetyl group, a dichloroacetyl group, a trichloroacetyl group, a trifluoroacetyl group and a benzoyl group. Among all, acyl groups having from 2 to 10 carbon atoms are preferable and an acetyl group or a benzoyl group is still preferable.

The protective groups for the hydroxyl groups other than the one at the anomeric position may be independently exemplified by acyl groups and optionally substituted alkyl groups. Examples of the acyl groups include those cited above. Examples of the optionally substituted alkyl groups include alkyl groups having from 1 to 10 carbon atoms optionally substituted by a substituent which is inactive during the reaction such as a halogen atom, an alkyl group, an aryl group or an alkoxy group. Among all, a benzyl group or an acyl group is preferable and an acyl group is still preferable.

As the pentose, a compound represented by the general formula (C), wherein $R^2$ to $R^{2'''}$ each represent an acyl group, is preferable.

$R^2$ to $R^{2'''}$ may be either the same or different from each other. It is preferable that at least those other than the one at the anomeric position are the same. It is particularly preferable that all of the groups at 4 positions are acetyl groups, or the one at the anomeric position is an acetyl group while others are all benzoyl groups.

The pentose may be isomerized at the anomeric position and then the isomer having the desired stereoconfiguration may be employed in the condensation reaction.

The pentose can be obtained by a conventional method for protecting hydroxyl groups. It is preferable to use a method comprising reacting a pentose unprotected at hydroxyl groups with an alcohol in the presence of an acid catalyst to give a pentose alkoxylated at the 1-position, then protecting the hydroxyl groups in a conventional manner, and then converting the alkoxy group at the 1-position into an acyloxy group. In this method, the product may be used after purification by column chromatography, recrystallization, re-precipitation, distillation or the like. Alternatively, the crude product may be used as such.

(Isomerization of Pentose)

To isomerize the pentose, use may be made of a method of isomerizing it in the presence of an acid anhydride and a sulfonic acid.

The acid anhydride to be used in the isomerization is a compound represented by $R^2_2O$ wherein $R^2$ has the same meaning as in the general formula (C). Specific examples thereof include acetic anhydride, propionic anhydride, butyric anhydride, monochloroacetic anhydride, dichloroacetic anhydride, trichloroacetic anhydride, trifluoroacetic anhydride and benzoic anhydride. Among these compounds, acetic anhydride or benzoic anhydride is preferable and acetic anhydride is still preferable since it can be industrially obtained at a low price.

The optimum amount of the acid anhydride employed varies depending on the combination of the pentose, the acid anhydride, the sulfonic acid and a solvent. In usual, it is employed in an amount 0.01 time by mol or more, preferably 0.1 time by mol or more, as much as the pentose. To reduce side-reactions, it is employed usually in an amount not more than 15 times by mol, preferably not more than 10 times by mol.

The sulfonic acid to be used in the isomerization of the pentose is not particularly restricted. Specific examples thereof include sulfuric acid, methanesulfonic acid, trifluoromethanesulfonic acid, ethanesulfonic acid, propanesulfonic acid, butanesulfonic acid, pentanesulfonic acid, hexanesulfonic acid, benzenesulfonic acid, p-toluenesulfonic acid, 1-naphthalenesulfonic acid and 2-naphthalenesulfonic acid. Among these sulfonic acids, those having pKa of −1 or below are preferable and sulfuric acid, methanesulfonic acid, trifluoromethanesulfonic acid and p-toluenesulfonic acid are still preferable. It is particularly preferable to use sulfuric acid, methanesulfonic acid or p-toluenesulfonic acid which can be industrially available at a low price.

The optimum amount of the sulfonic acid employed varies depending on the combination of the pentose, the acid anhydride and a solvent. In usual, it is employed in an amount 0.01 time by mol or more, preferably 0.1 time by mol or more, as much as the pentose. Use of the sulfonic acid in excess might induce the decomposition of the compounds. Therefore, it is usually used in an amount not more than 5 times by mol, preferably not more than 1.5 times by mol.

In the isomerization, a solvent is usually employed. The solvent is not particularly restricted, so long as the pentose, the acid anhydride and the sulfonic acid are soluble therein. Specific examples thereof include carboxylic acids represented by $R^2OH$, wherein $R^2$ is as defined in the general formula (C), such as acetic acid, propionic acid, butyric acid, monochloroacetic acid, dichloroacetic acid, trichloroacetic acid, trifluoroacetic acid and benzoic acid; aromatic hydrocarbons such as benzene, toluene and xylene; halogenated aromatic hydrocarbons such as chlorobenzene and dichlorobenzene; aliphatic hydrocarbons such as hexane, heptane and octane; halogenated hydrocarbons such as dichloroethane, chloroform and 1,2-dichloroethane; ethers such as diethyl ether, di-n-propyl ether, diisopropyl ether, di-n-butyl ether, tert-butyl methyl ether, THF and 1,4-dioxane; ketones such as acetone, ethyl methyl ketone and isobutyl methyl ketone; esters such as ethyl acetate, n-propyl acetate, isopropyl acetate and n-butyl acetate; and acetonitrile. It is also possible to use a mixture of two or more of these solvents.

Among all, carboxylic acids are preferable since pentoses show high solubility therein. In particular, acetic acid which can be obtained at a low price is preferable.

The solvent may be used in such an amount that the reaction mixture can be stirred. In usual, the solvent is used in an amount from 1 to 100 times by weight, preferably from 2 to 30 times by weight, as much as the pentose.

The isomerization of the pentose can be carried out in an arbitrary reaction mode. It is preferable to add the sulfonic acid to a solution of the pentose and the acid anhydride under stirring and then reacting therewith, or to add the pentose to a solution of the sulfonic acid and the acid anhydride under stirring.

In the isomerization, a thermodynamically stable isomer is preferentially formed in usual. In case of ribose, in particular, an isomer having the substituents at the 1- and 2-positions in the trans-configuration is preferentially formed.

To inhibit the decomposition of the compounds, the reaction temperature is controlled usually to 150° C. or below, preferably to 100° C. or below. However, an excessively low reaction temperature is not efficient, since it results in a low reaction rate. Therefore, the reaction is carried out usually at −20° C. or above, preferably 0° C. or above.

The reaction time varies depending on the pentose, the acid anhydride, the sulfonic acid and the solvent type. The reaction initiates immediately after mixing and is completed usually within 12 hours.

Although the reaction is usually carried out under atmospheric pressure, it may be carried out under elevated or reduced pressure, if needed.

Although the reaction may be carried out in air, it is preferable to carry out the reaction in the atmosphere of an inert gas such as nitrogen or argon so as to prevent the acid anhydride from decomposition due to moisture absorption.

After the completion of the isomerization, the pentose can be taken out as crystals by cooling the liquid reaction mixture as such, or adding a poor solvent to the liquid reaction mixture. Alternatively, the pentose can be isolated by, after the completion of the reaction, adding water, extracting, washing and concentrating.

In case where it is desired to obtain a 1,2-cis isomer, it can be recovered from the mother liquor after separating the 1,2-trans isomer with a high crystallinity by the crystallization as described above.

It is also possible to further subject a pentose-containing solution having configurations other than the desired one (for example, the mother liquor after the crystallization as described above) to the isomerization reaction to thereby elevate the yield of the pentose having the desired configuration.

The pentose thus isolated may be further purified by a commonly employed purification method, for example, recrystallization, re-precipitation or column chromatography to thereby give pentose having a higher purity.

(Iron Halide)

Examples of the iron halide to be used in the process according to the invention include $FeCl_3$, $FeCl_2$, $FeBr_3$ and $FeBr_2$. These iron halides may be in the hydrate form. Among all, $FeCl_3$ is preferable and its anhydride is particularly preferable.

(Condensation Reaction)

In the process of the invention, the dinitrogen 6-membered heterocyclic compound or the trinitrogen 5-membered heterocyclic compound is brought into contact with the pentose in the presence of the iron halide.

The contact is not particularly restricted in procedure or order. In a typical case, for example, the pentose and the iron halide are successively added to a solution containing the silylated dinitrogen 6-membered heterocyclic compound or the trinitrogen 5-membered heterocyclic compound at room temperature or below and then the reaction is performed by heating to the reaction temperature.

The silylated dinitrogen 6-membered heterocyclic compound or the trinitrogen 5-membered heterocyclic compound may be employed in an arbitrary amount based on the pentose. It is usually preferable to use it in excess, since the silylated compound is decomposed by impurities such as water contained in the reaction system. More specifically speaking, it is usually employed in an amount of from 1.05 to 2 molar equivalents, preferably from 1.1 to 1.3 molar equivalents.

The iron halide is employed in an amount, based on the pentose, of usually 0.2 molar equivalent or more, preferably 0.5 molar equivalent or more, still preferably 0.8 molar equivalent or more and particularly preferably 1.0 molar equivalent or more. Although the reaction rate is elevated with an increase in the amount of the iron halide, it is employed in an amount of usually not more than 5 molar equivalents, preferably not more than 2 molar equivalents and particularly preferably not more than 1.5 molar equivalents, from the viewpoints of the removal of the catalyst residue and cost.

Examples of the solvent for the condensation reaction include aromatic hydrocarbons such as toluene, benzene and xylene; ether solvents such as methyl-t-butyl ether and tetrahydrofuran; halogenated hydrocarbons such as methylene chloride and chloroform; ester solvents such as methyl acetate and ethyl acetate; and nitrile solvents such as acetonitrile and propionitrile. Either one of these solvents or a mixture of two or more thereof may be used. Among all, it is preferable to use acetonitrile.

The solvent is employed in an amount from 0.5 to 50 times by volume, preferably from 1 to 30 times by volume, as much as the dinitrogen 6-membered heterocyclic compound or the trinitrogen 5-membered heterocyclic compound.

The reaction temperature may be set to an arbitrary level. From the viewpoint of the reaction rate, the reaction is usually carried out at 25° C. or above. In case where the temperature is too high, on the other hand, there arises a tendency toward the decomposition of the condensed product. Thus, the reaction is carried out usually at 80° C. or below, preferably 50° C. or below.

After the completion of the reaction, the reaction mixture is brought into contact with an alkaline aqueous solution to decompose the residual catalyst. Then the target compound is isolated by post-treatment procedures commonly employed, for example, extracting with an organic solvent, washing with a saturated aqueous solution of sodium chloride, drying over a dehydrating agent such as sodium sulfate and concentrating.

In the decomposition of the catalyst, it is preferable to cool the alkaline aqueous solution. It is also preferable to employ a procedure of adding the reaction mixture to the alkaline aqueous solution.

For the purification, use may be made of an arbitrary method such as column chromatography or crystallization. From an industrial viewpoint, it is preferable to employ the crystallization method.

The crystallization method may be arbitrarily selected from the methods commonly employed for crystallization, for example, a method wherein a crude product is dissolved in a good solvent and then cooled by allowing to stand or using a cryogenic liquid, a method wherein a poor solvent is added, or a method of combining them.

Examples of the poor solvent usable herein include aliphatic hydrocarbon solvents such as pentane, hexane and heptane. Among all, it is preferable to use hexane or heptane.

Examples of the good solvent usable herein include aromatic hydrocarbon solvents such as toluene, benzene and xylene; ether solvents such as methyl-t-butyl ether and tetrahydrofuran; halogenated hydrocarbon solvents such as methylene chloride and chloroform; ester solvents such as methyl acetate and ethyl acetate; and nitrile solvents such as acetonitrile and propionitrile. Among all, it is preferable to use toluene, tetrahydrofuran, ethyl acetate or acetonitrile.

The poor solvent is employed in an amount usually from 0.1 to 50 times by volume, preferably from 0.5 to 30 times by volume, as much as the condensed product.

After the crystallization, the product is filtered, washed and dried by procedures commonly employed and thus isolated as a white powder.

The condensed product thus obtained may be further used to the deprotection of the hydroxyl groups and derived, if needed.

As the deprotection reaction, use can be made of usual deacylation reactions, for example, treating in an ammonia-methanol solution.

EXAMPLES

Now, the invention will be described in greater detail by reference to the following EXAMPLES. However, it is to be understood that the invention is not construed as being restricted thereto.

Production Example 1

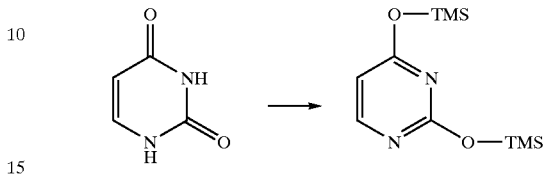

5.6 g of uracil and 0.1 g of ammonium sulfate were dissolved in 22.4 ml of 1,1,1,3,3,3-hexamethyldisilazane and reacted at 120° C. for 2.5 hours. After the completion of the reaction, the reaction mixture was distilled to give 11.8 g of 2,4-bis(trimethylsilyloxy)-1,3-diazine. $^1$H-NMR (400 MHz, in $C_2D_6CO$): δ=0.29 (s, 9H), 0.31 (s, 9H), 6.35 (d, J=5.6 Hz, 1H), 8.19 (d, J=5.5Hz, 1H)

Referential Example 1

1.21 g of 2,4-bis(trimethylsilyloxy)-1,3-diazine obtained in PRODUCTION EXAMPLE 1 and 1.15 g of 1,2,3,5-tetra-O-acetyl-β-D-ribofuranose were dissolved in 4.8 ml of acetonitrile and cooled to 5° C. Next, 0.94 g of $SnCl_4$ was added dropwise thereinto at the same temperature. After stirring for 10 minutes at the same temperature, the mixture was heated to 50° C. and reacted for 3 hours. The reaction mixture was analyzed by HPLC. Thus, β-uridine triacetate was obtained with a reaction yield of 83%.

Example 1

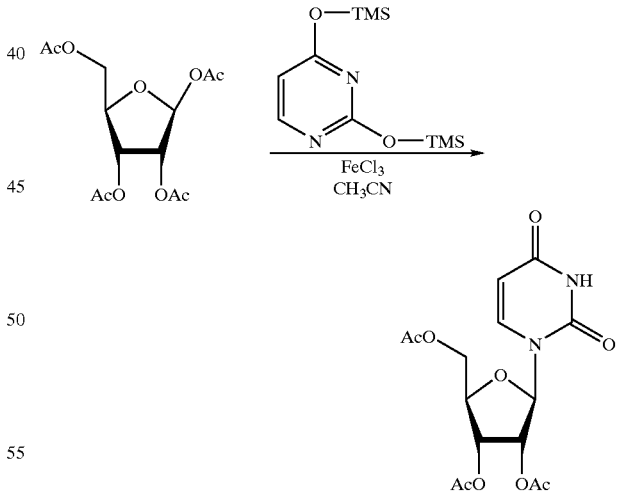

0.93 g of 2,4-bis(trimethylsilyloxy)-1,3-diazine obtained in PRODUCTION EXAMPLE 1 and 0.92 g of 1,2,3,5-tetra-O-acetyl-β-D-ribofuranose were dissolved in 4.7 ml of acetonitrile and cooled to 4° C. Then 0.49 g of $FeCl_3$ was added thereto at the same temperature. After stirring for 10 minutes at the same temperature, the mixture was heated to 50° C. and reacted. The reaction was monitored by HPLC. After the completion of the reaction, the reaction mixture was added dropwise at 4° C. into a cold aqueous solution of sodium hydrogencarbonate which had been preliminarily prepared. After filtering off the catalyst residue, the filtrate was separated and the aqueous layer was extracted with 20 ml portions of ethyl acetate thrice. The organic layers were combined, washed with a saturated aqueous solution of sodium chloride and dried over sodium sulfate. After distilling off the solvent, 1.2 g (purity 80%) of the target compound was obtained as a viscous white solid.

Namely, the target compound could be obtained at a yield comparable to REFERNTIAL EXAMPLE 1 wherein SnCl$_4$ was employed as the catalyst. $^1$H-NMR (400 MHz, in CDCl$_3$): δ=2.11 (s, 3H), 2.14 (s, 3H), 2.15 (s, 3H), 4.35 (m, 3H), 5.33 (m, 2H), 5.79 (d, J=8.2 Hz, 1H), 6.04 (d, J=4.9 Hz, 1H), 7.39 (d, J=8.2 Hz, 1H)

Example 2

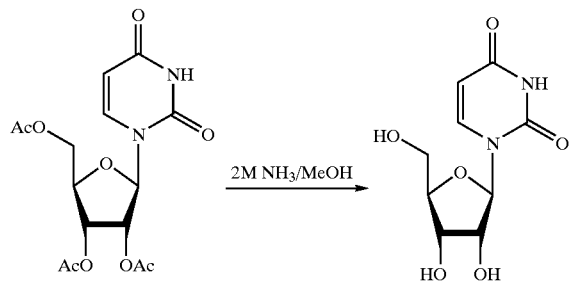

1.2 g (purity 80%) of uridine triacetate obtained in EXAMPLE 1 was dissolved in 9.4 ml of a 2 M ammonia methanol solution and stirred at room temperature (23° C.). After the completion of the reaction, the solvent was distilled off to give 0.7 g of crude uridine (purity 87%) as a white solid. Ethanol in an amount 48.5 times by volume as much as the crude uridine was added and uridine was completely dissolved herein by heating to 58° C. Next, the solution was allowed to cool to room temperature (23° C.) and aged for 30 minutes. Then, it was cooled to 5° C. and aged for 30 minutes. The precipitated white crystals were filtered, washed and dried to give 0.3 g of β-uridine (purity 97%). $^1$H-NMR (400 MHz, in D$_2$O): δ=3.76 (dd, J=12.6, 4.3 Hz, 1H), 3.87 (dd, J=12.6, 2.8 Hz, 1H), 4.09 (m, 1H), 4.18 (m, 1H), 4.31 (m, 1H), 5.86 (m, 1H), 7.83 (d, J=8.1 Hz, 1H)

Example 3

5.6 g of uracil and 0.1 g of ammonium sulfate were dissolved in 2.4 ml of 1,1,1,3,3,3-hexamethyldisilazane and reacted at 120° C. for 2.5 hours. After the completion of the reaction, 1,1,1,3,3,3-hexamethyldisilazane was distilled off to give 12.8 g of crude 2,4-bis(trimethylsilyloxy)-1,3-diazine. A 0.59 g portion of this compound was taken and dissolved together with 0.61 g of 1,2,3,5-tetra-O-acetyl-β-D-ribofuranose in 2.5 ml of acetonitrile. After cooling to 2° C., 0.31 g of FeCl$_3$ was added thereto. After stirring at the same temperature for 10 minutes, the mixture was heated to 50° C. and reacted. The reaction was monitored by HPLC. Thus it was confirmed that β-uridine triacetate was obtained with a reaction yield of 97% after reacting for 2 hours.

Example 4

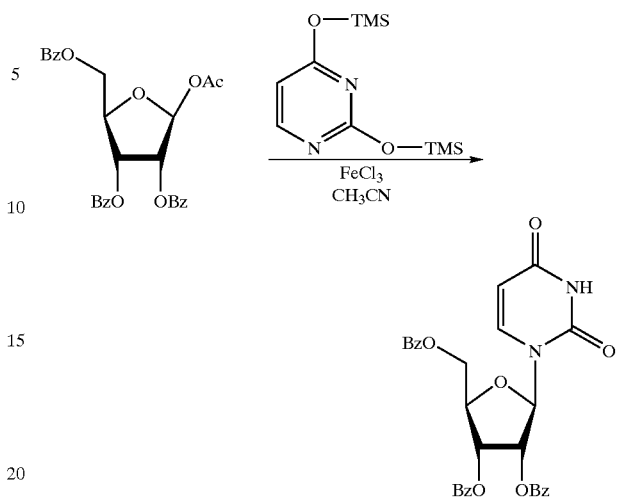

0.49 g of 2,4-bis(trimethylsilyloxy)-1,3-diazine obtained in PRODUCTION EXAMPLE 1 and 0.80 g of 1-O-acetyl-2,3,5-tri-O-benzoylacetyl-β-D-ribofuranose were dissolved in 2.5 ml of acetonitrile and cooled to 2° C. Then 0.26 g of FeCl$_3$ was added thereto. After stirring for 10 minutes at the same temperature, the mixture was heated to 50° C. and reacted. The reaction was monitored by HPLC. Thus it was confirmed that β-uridine tribenzoate was obtained with a reaction yield of 96% after reacting for 1 hour. $^1$H-NMR (400 MHz, in CDCl$_3$): δ=4.66–4.83 (m, 3H), 5.62 (d, J=5.8 Hz, 1H), 5.76 (t, J=4.5 Hz, 1H), 5.89 (t, J=3.6 Hz, 1H), 6.32 (d, J=5.6 Hz, 1H), 7.26 –8.11 (m, 15H), 8.38 (s, 1H)

Example 5

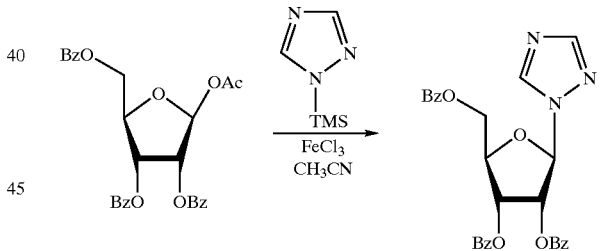

584 mg of 1,2,4-triazole and 34 mg of ammonium sulfate were dissolved in 3.55 ml of 1,1,1,3,3,3-hexamethyldisilazane and reacted at 120° C. for 2.5 hours. After the completion of the reaction, 1,1,1,3,3,3-hexamethyldisilazane was distilled off to give 1.21 g of crude silylated 1,2,4-triazole. This silylated triazole and 3.88 g of 1-O-acetyl-2,3,5-tri-O-benzoyl-β-D-ribofuranose were dissolved in 8 ml of acetonitrile. After cooling to 3° C., 1.35 g of FeCl$_3$ was added thereto. After stirring at the same temperature for 5 minutes, the mixture was heated to 50° C. and reacted. The reaction was monitored by HPLC. Thus it was confirmed that the target compound was obtained with a reaction yield of 77% after reacting for 2 hours.

$^1$H-NMR (400 MHz, in CDCl$_3$): δ=4.61 (dd, J=12, 5.0 Hz, 1H), 4.81 (dd, J=12.3, 3.8 Hz, 1H), 4.88 (m, 1H), 6.12 (m, 1H), 6.23 (d, J=6.8 Hz, 1H), 6.26 (d, 1.8 Hz, 1H), 7.38 (m, 6H), 7.42 (m, 3H), 8.00 (m, 5H), 8.05 (d, J=7.2 Hz, 2H), 8.31 (s, 1H)

Example 6

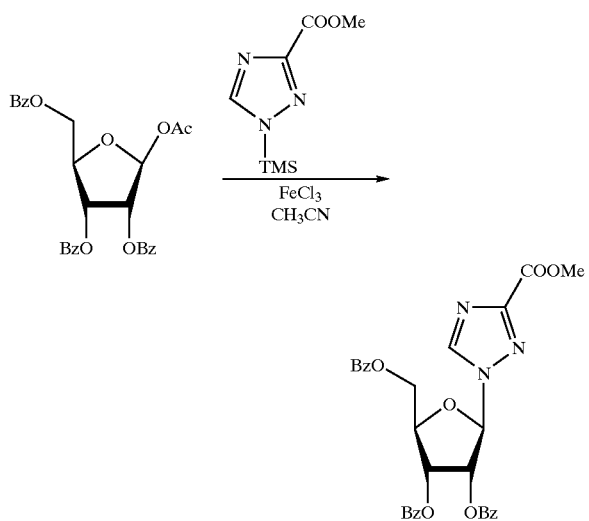

1.08 g of 1,2,4-triazole-3-methylcarboxylate and 34 mg of ammonium sulfate were dissolved in 3.55 ml of 1,1,1,3,3,3-hexamethyldisilazane and reacted at 120° C. for 2.5 hours. After the completion of the reaction, 1,1,1,3,3,3-hexamethyldisilazane was distilled off to give 1.90 g of crude silylated 1,2,4-triazole-3-methylcarboxylate. A 0.95 g portion of this compound was taken and dissolved together with 1.94 g of 1-O-acetyl-2,3,5-tri-O-benzoyl-β-D-ribofuranose in 4 ml of acetonitrile. After cooling to 3° C., 0.75 g of FeCl$_3$ was added thereto. After stirring at the same temperature for 5 minutes, the mixture was heated to 50° C. and reacted. The reaction was monitored by HPLC. Thus it was confirmed that the target compound was obtained with a reaction yield of 54% after reacting for 2 hours. $^1$H-NMR (400 MHz, in CDCl$_3$): δ=3.98 (s, 3H), 4.66 (dd, J=12, 4.6 Hz, 1H), 4.82 (dd, J=16, 3.3 Hz, 1H), 4.89 (m, 1H), 6.10 (m, 1H), 6.16 (m, 1H), 6.33 (d, 1.5 Hz, 1H), 7.41 (m, 6H), 7.57 (m, 3H), 7.94 (m, 5H), 8.06 (d, J=7.1 Hz, 2H), 8.42 (s, 1H)

Production Example 2

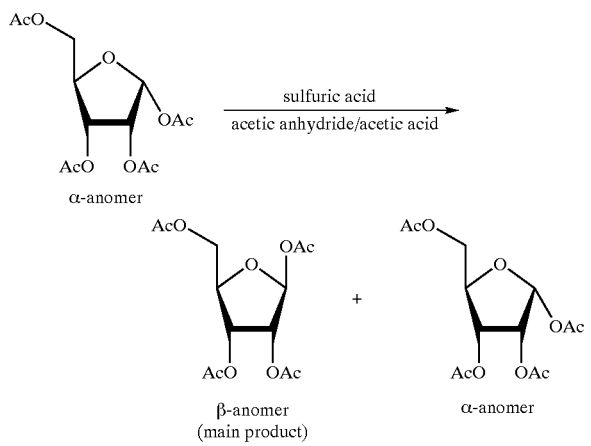

To 0.10 g (0.3 mmol) of 1,2,3,5-tetra-O-acetyl-α-D-ribofuranose were added 0.16 g (2.7 mmol) of acetic acid and 0.21 g (2.1 mmol) of acetic anhydride. The obtained solution was cooled by putting into an ice-bath and 0.02 g (0.2 mmol) of conc. sulfuric acid was added dropwise thereinto. After the completion of the addition, the mixture was taken out from the ice-bath and stirred at room temperature for 2 hours. Then the reaction mixture was neutralized and analyzed by capillary GC. As a result, the α-anomer and the β-anomer were observed at a ratio of 26:74 with little any other by-products.

The β-anomer which was the isomerized product could be efficiently obtained by adding water to the liquid reaction mixture, extracting with an organic solvent and then separating by crystallization from the resultant solution.

Production Example 3

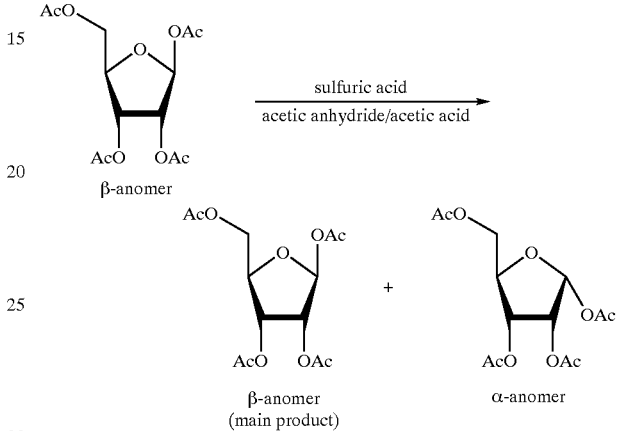

To 0.19 g (0.6 mmol) of 1,2,3,5-tetra-O-acetyl-β-ribofuranose were added 0.29 g (4.8 mmol) of acetic acid and 0.40 g (3.9 mmol) of acetic anhydride. The obtained solution was cooled by putting into an ice-bath and 0.01 g (0.1 mmol) of conc. sulfuric acid was added dropwise thereinto. After the completion of the addition, the mixture was taken out from the ice-bath and stirred at room temperature for 4.5 hours. Then the reaction mixture was neutralized and analyzed by capillary GC. As a result, the α-anomer and the β-anomer were observed at a ratio of 25:75 with little any other by-products.

The α-anomer which was the isomerized product could be efficiently obtained from the mother liquor after carrying out the post-treatment procedures and separating the β-anomer by crystallization as in PRODUCTION EXAMPLE 2.

Production Example 4

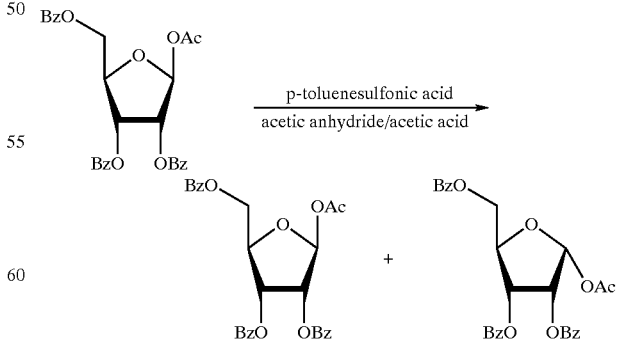

To a solution of 0.21 g (0.4 mmol) of 1-O-acetyl-2,3,5-tri-O-benzoyl-β-D-ribofuranose in 0.56 g (9.3 mmol) of acetic acid and 0.08 g (0.8 mmol) of acetic anhydride was added 0.01 g (0.05 mmol) of p-toluenesulfonic acid monohydrate. Then the resultant mixture was stirred at 90° C. for 1.5 hours. Then the reaction mixture was analyzed by HPLC. As a result, the α-anomer and the β-anomer were observed at a ratio of 35:65 with little any other by-products.

The α-anomer which was the isomerized product could be efficiently obtained from the mother liquor after carrying out the post-treatments and separating the β-anomer by crystallization as in EXAMPLE 1.

Referential Example 2

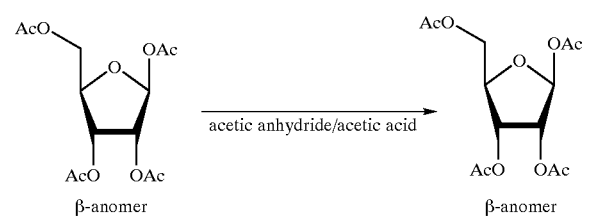

To 0.19 g (0.6 mmol) of 1,2,3,5-tetra-O-acetyl-β-D-ribofuranose were added 0.29 g (4.8 mmol) of acetic acid and 0.40 g (3.9 mmol) of acetic anhydride and the resultant mixture was stirred at room temperature for 5.5 hours. Then the liquid reaction mixture was neutralized and analyzed by capillary GC. As a result, nothing but the β-anomer was detected.

According to the process of the invention, an efficient condensation process by using a less expensive and safe reagent can be provided in producing a nucleic acid derivative by condensing a specific nitrogen-containing heterocyclic compound such as a dinitrogen 6-membered heterocyclic compound or a trinitrogen 5-membered heterocyclic compound with a pentose.

While the invention has been described in detail and with reference to specific embodiments thereof, it will be apparent to one skilled in the art that various changes and modifications can be made therein without departing from the scope thereof.

This application is based on Japanese patent applications No. 2002-033514 filed Feb. 12, 2002 and No. 2002-036204 filed Feb. 14, 2002, the entire contents thereof being hereby incorporated by reference.

What is claimed is:

1. A process for producing a nucleic acid derivative, which comprises condensing a dinitrogen 6-membered heterocyclic compound or a trinitrogen 5-membered heterocyclic compound with a pentose in the presence of an iron halide; wherein the dinitrogen 6-membered heterocyclic compound is a compound represented by the following formula (A) or (A'):

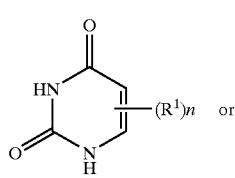

(A)

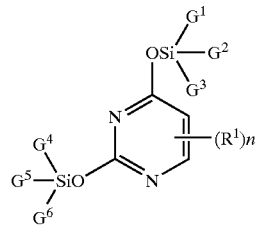

(A')

wherein $R^1$ represents a halogen atom, a cyano group, a carboxylic ester group, carbamoyl group, a formyl group, an acyl group, an amino group or an alkyl group; $G^1$, $G^2$, $G^3$, $G^4$, $G^5$ and $G^6$ each independently represent an alkyl group; and n is an integer of 0 to 2, provided that in case where n is 2, a plural number of $R^1$s may be different from each other, and two $R^1$s adjacent to each other may form together a carbon ring or a heterocycle; and the trinitrogen 5-membered heterocyclic compound is a compound represented by the following formula (B) or (B');

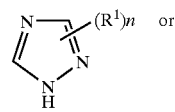

(B)

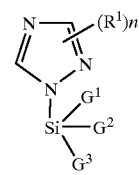

(B')

wherein $R^1$, $G^1$, $G^2$, $G^3$ and n are each as defined above; and wherein the pentose is a compound represented by the following formula (C):

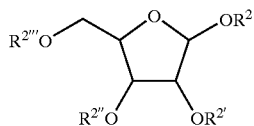

(C)

wherein $R^2$ to $R^{2'''}$ each independently represent an acyl group.

2. The process according to claim 1, which comprises treating a compound represented by the formula (A) or (B) with a silylating agent to give a compound represented by the formula (A') or (B') and subsequently condensing it with a pentose in the presence of an iron halide.

3. The process according to claim 1 wherein the pentose is a compound represented by the following formula (D) or (D'):

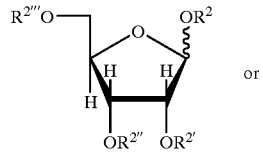

(D)

-continued

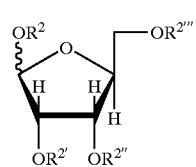
(D')

wherein $R^2$ to $R^{2'''}$ are each as defined in claim 1.

4. The production process according to claim 1, wherein the iron halide employed is $FeCl_3$.

5. The process according to claim 1, wherein the pentose is isomerized at the anomeric position in the presence of an acid anhydride and a sulfonic acid to achieve a pentose in the β-anomer configuration and then subjected to the condensation reaction.

6. The process according to claim 1 which further comprises subjecting a nucleic acid derivative obtained to a deacylation reaction at the hydroxyl moiety in a saccharide residue of the nucleic acid derivative.

7. The process according to claim 6, wherein a compound represented by the following formula (E):

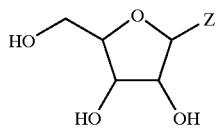
(E)

wherein Z represents a group derived from a dinitrogen 6-membered heterocyclic compound or a trinitrogen 5-membered heterocyclic compound in which the nitrogen atom constituting the ring serves as the bonding position; is produced.

8. The process according to claim 7, wherein Z is a group represented by the following formula (A"):

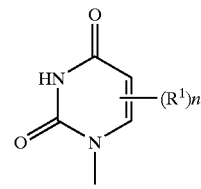
(A")

wherein $R^1$ represents a halogen atom, a cyano group, a carboxylic ester group, carbamoyl group, a formyl group, an acyl group, an amino group or an alkyl group; and n is an integer of 0 to 2, provided that in case where n is 2, a plural number of $R^1$s may be different from each other, and two $R^1$s adjacent to each other may form together a carbon ring or a heterocycle;

or a group represented by the following formula (B"):

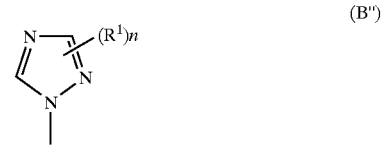
(B")

wherein $R^1$ and n are each as defined above.

9. The process according to claim 2, which further comprises subjecting a nucleic acid derivative obtained to a deacylation reaction at the hydroxyl moiety in a saccharide residue of the nucleic acid derivative.

10. The process according to claim 3, which further comprises subjecting a nucleic acid derivative obtained to a deacylation reaction at the hydroxyl moiety in a saccharide residue of the nucleic acid derivative.

11. The process according to claim 4, which further comprises subjecting a nucleic acid derivative obtained to a deacylation reaction at the hydroxyl moiety in a saccharide residue of the nucleic acid derivative.

12. The process according to claim 5, which further comprises subjecting a nucleic acid derivative obtained to a deacylation reaction at the hydroxyl moiety in a saccharide residue of the nucleic acid derivative.

* * * * *